United States Patent
Porter et al.

(10) Patent No.: US 9,622,751 B2
(45) Date of Patent: Apr. 18, 2017

(54) VASO-OCCLUSIVE DEVICES WITH TEXTURED SURFACES

(75) Inventors: Stephen C. Porter, Oakland, CA (US); Like Que, Livermore, CA (US); Tri D. Tran, Fountain Valley, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1728 days.

(21) Appl. No.: 12/462,663

(22) Filed: Aug. 6, 2009

(65) Prior Publication Data

US 2010/0036412 A1    Feb. 11, 2010

Related U.S. Application Data

(60) Provisional application No. 61/188,096, filed on Aug. 6, 2008.

(51) Int. Cl.
*A61M 29/00* (2006.01)
*A61B 17/12* (2006.01)
*A61B 17/00* (2006.01)

(52) U.S. Cl.
CPC .. *A61B 17/12022* (2013.01); *A61B 17/12113* (2013.01); *A61B 17/12145* (2013.01); *A61B 17/12154* (2013.01); *A61B 2017/00858* (2013.01)

(58) Field of Classification Search
CPC . A61B 17/12109; A61B 17/1215; A61F 2/01; A61F 2230/0008
USPC .......................... 606/191, 200; 128/831, 843
See application file for complete search history.

(56) References Cited

U.S. PATENT DOCUMENTS

| | | | |
|---|---|---|---|
| 3,174,851 A | 3/1965 | Buehler | |
| 3,351,463 A | 11/1967 | Rozner | |
| 3,753,700 A | 8/1973 | Harrison et al. | |
| 4,739,768 A | 4/1988 | Engelson | |
| 4,994,069 A | 2/1991 | Ritchart et al. | |
| 5,122,136 A | 6/1992 | Guglielmi et al. | |
| 5,290,552 A | 3/1994 | Sierra et al. | |
| 5,354,295 A | 10/1994 | Guglielmi et al. | |
| 5,382,259 A | 1/1995 | Phelps et al. | |
| 5,582,619 A | 12/1996 | Ken | |
| 5,658,308 A * | 8/1997 | Snyder ......................... | 606/191 |
| 5,690,666 A | 11/1997 | Berenstein et al. | |
| 5,792,154 A | 8/1998 | Doan et al. | |
| 5,826,587 A | 10/1998 | Berenstein et al. | |
| 5,833,705 A | 11/1998 | Ken et al. | |
| 5,853,418 A | 12/1998 | Ken et al. | |
| 5,935,145 A | 8/1999 | Villar et al. | |

(Continued)

FOREIGN PATENT DOCUMENTS

| | | |
|---|---|---|
| EP | 1266631 | 12/2002 |
| WO | 94/10936 | 5/1994 |

(Continued)

OTHER PUBLICATIONS

International Search Report and Written Opinion for International Application No. PCT/US2009/004523 filed on Aug. 6, 2009, search report mailed on Oct. 29, 2009. (17 pages).

*Primary Examiner* — Elizabeth Houston
*Assistant Examiner* — L Bachman

(57) ABSTRACT

Disclosed herein are vaso-occlusive devices for forming occluding the vasculature of a patient. More particularly, disclosed herein are vaso-occlusive devices having a textured outer surface for promoting tissue in-growth.

10 Claims, 11 Drawing Sheets

(56) References Cited

U.S. PATENT DOCUMENTS

| | | |
|---|---|---|
| 6,001,092 A | 12/1999 | Mirigian et al. |
| 6,004,338 A | 12/1999 | Ken et al. |
| 6,013,084 A | 1/2000 | Ken et al. |
| 6,033,423 A | 3/2000 | Ken et al. |
| 6,159,165 A | 12/2000 | Ferrera et al. |
| 6,168,788 B1 | 1/2001 | Wortham |
| 6,179,857 B1 | 1/2001 | Diaz et al. |
| 6,193,728 B1 | 2/2001 | Ken et al. |
| 6,280,457 B1 | 8/2001 | Wallace et al. |
| 6,287,318 B1 | 9/2001 | Villar et al. |
| 6,299,627 B1 | 10/2001 | Eder et al. |
| 6,458,119 B1 | 10/2002 | Berenstein et al. |
| 6,533,801 B2 | 3/2003 | Wallace et al. |
| 6,569,179 B2 * | 5/2003 | Teoh et al. .................. 606/191 |
| 6,585,754 B2 | 7/2003 | Wallace et al. |
| 6,623,493 B2 | 9/2003 | Wallace et al. |
| 6,635,069 B1 | 10/2003 | Teoh et al. |
| 6,929,654 B2 | 8/2005 | Teoh et al. |
| 6,953,468 B2 | 10/2005 | Jones et al. |
| 2004/0106946 A1 | 6/2004 | Ferrera et al. |
| 2004/0153025 A1* | 8/2004 | Seifert et al. .................. 604/19 |
| 2004/0211429 A1* | 10/2004 | Nikolchev et al. .......... 128/831 |
| 2005/0209633 A1* | 9/2005 | Callister et al. ............. 606/200 |
| 2005/0240216 A1* | 10/2005 | Jones et al. .................. 606/200 |
| 2005/0267510 A1* | 12/2005 | Razack ........................ 606/200 |
| 2006/0079926 A1* | 4/2006 | Desai et al. .................. 606/200 |

FOREIGN PATENT DOCUMENTS

| | | |
|---|---|---|
| WO | 99/40852 | 8/1999 |
| WO | 00/12016 | 3/2000 |
| WO | 00/74577 | 12/2000 |
| WO | WO 02/45596 A2 | 6/2002 |
| WO | WO 02/051460 A2 | 7/2002 |
| WO | 02/096272 | 12/2002 |
| WO | 03/039376 | 5/2003 |

* cited by examiner

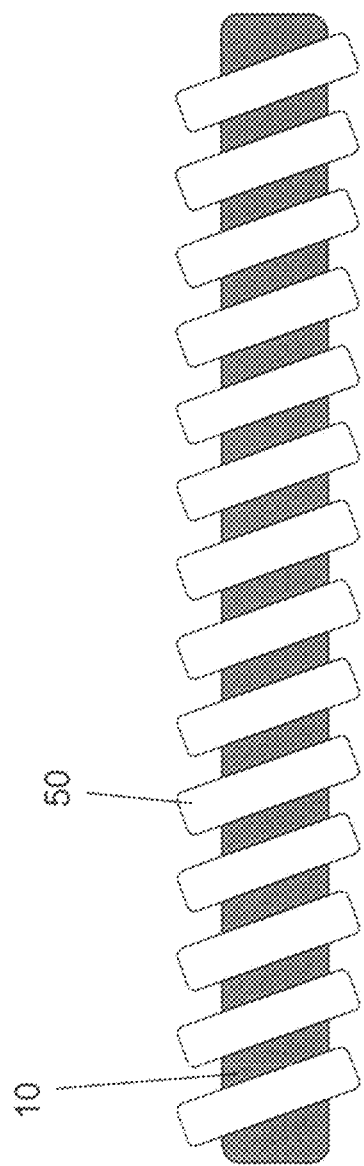
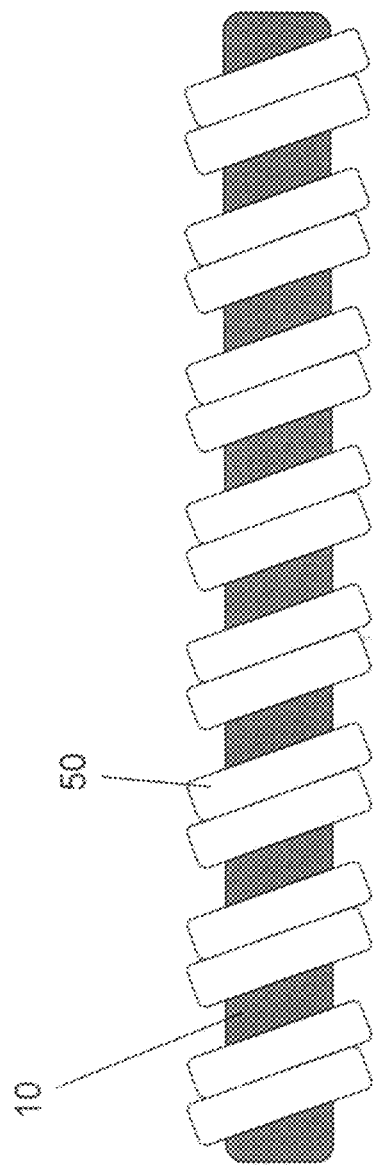

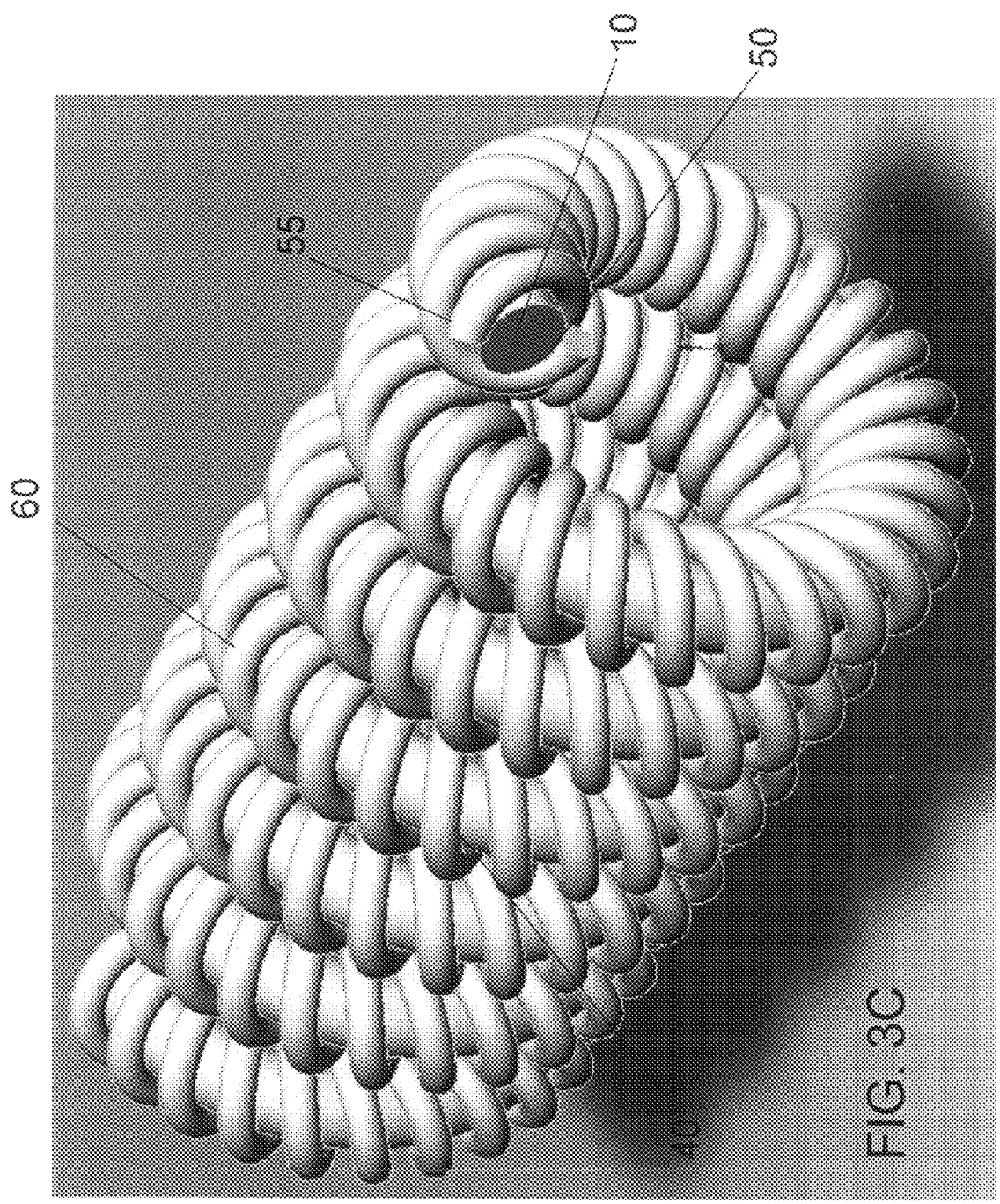

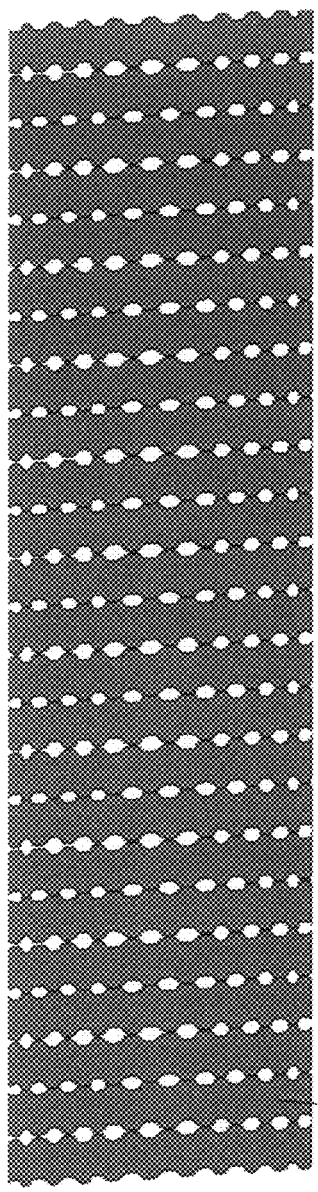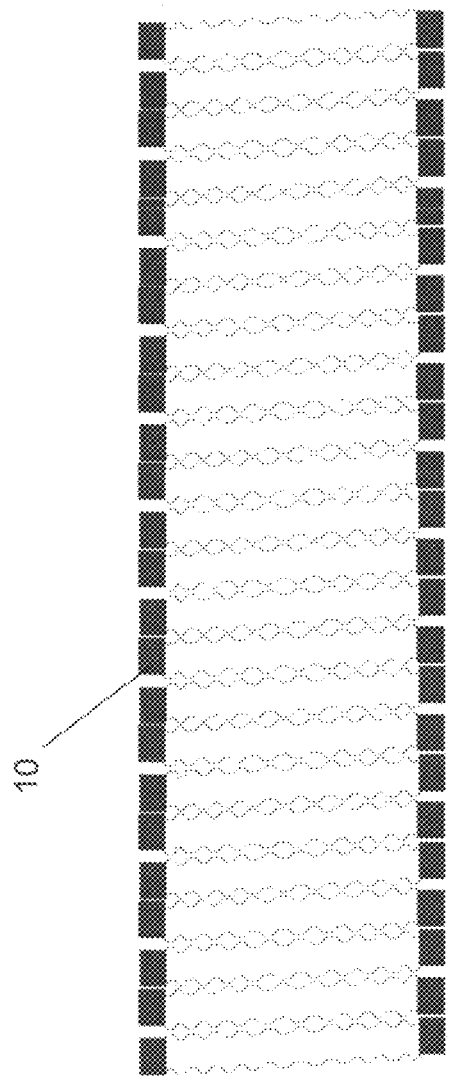

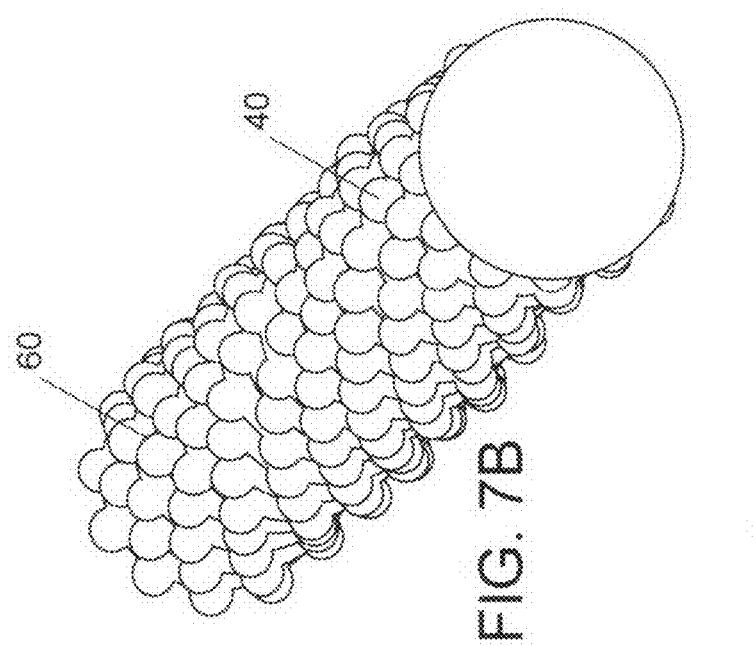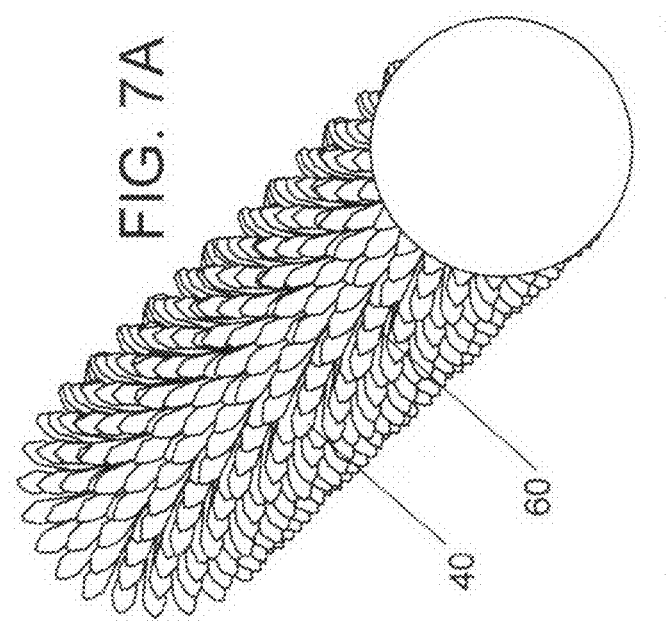

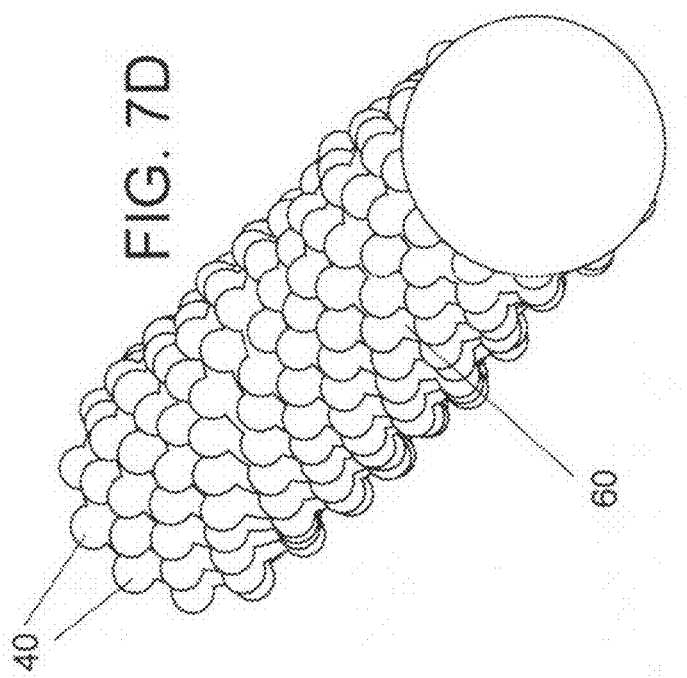
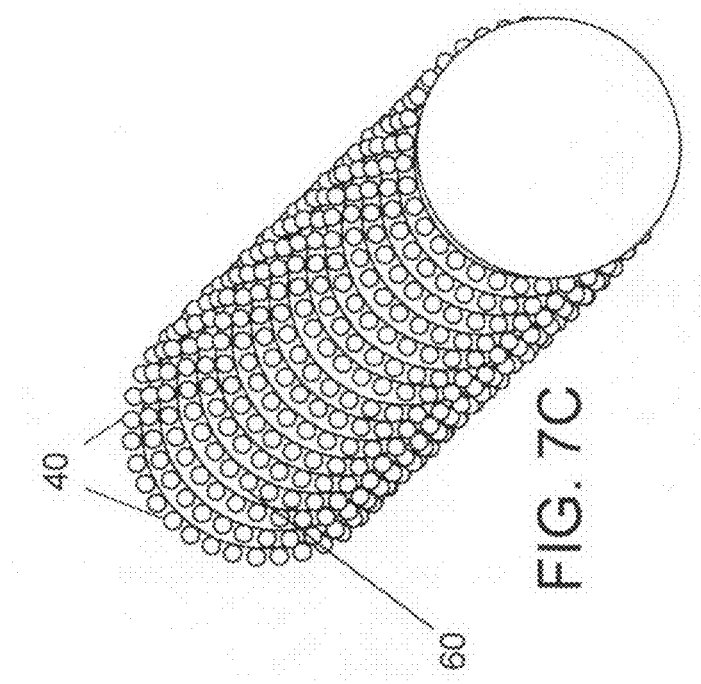

VASO-OCCLUSIVE DEVICES WITH TEXTURED SURFACES

CROSS-REFERENCE TO RELATED APPLICATIONS

This application claims the benefit of U.S. provisional patent application No. 61/188,096, filed Aug. 6, 2008, the disclosure of which is incorporated by reference in its entirety for all purposes.

FIELD OF THE INVENTION

Compositions and methods for repair of aneurysms are described. In particular, vaso-occlusive devices having a non-random, textured outer surface are disclosed, as are methods of making and using these devices.

BACKGROUND

An aneurysm is a dilation of a blood vessel that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of aneurysms, including platinum and stainless steel microcoils, polyvinyl alcohol sponges (Ivalone), and other mechanical devices. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings that may be dimensioned to engage the walls of the vessels. (See, e.g., U.S. Pat. No. 4,994,069 to Ritchart et al.). Electrolytically detachable embolic devices have also been described (U.S. Pat. No. 5,354,295 and its parent, U.S. Pat. No. 5,122,136) as well as vaso-occlusive coils having little or no inherent secondary shape have also been described (see, e.g., co-owned U.S. Pat. Nos. 5,690,666; 5,826,587; and 6,458,119). In addition, multi-stranded microcoils are disclosed in U.S. Pat. No. 6,159,165.

Coil designs including stretch-resistant members that run through the lumen of the helical vaso-occlusive coil have also been described. See, e.g., U.S. Pat. Nos. 5,582,619; 5,833,705; 5,853,418; 6,004,338; 6,013,084; 6,179,857; and 6,193,728.

In addition, coil devices including polymer coatings or attached polymeric filaments have also been described. See, e.g., U.S. Pat. No. 5,658,308; 5,792,154; 5,935,145; 6,001, 092; 6,033,423; 6,280,457; 6,287,318; and 6,299,627. For instance, U.S. Pat. No. 6,280,457 describes wire vaso-occlusive coils having single or multi-filament polymer coatings. U.S. Pat. Nos. 6,287,318 and 5,935,145 describe metallic vaso-occlusive devices having a braided polymeric component attached thereto. U.S. Pat. No. 5,382,259 describes braids covering a primary coil structure.

However, there remains a need for vaso-occlusive devices comprising textured outer surfaces as described herein, or methods of making and using such devices.

SUMMARY OF THE INVENTION

Thus, this invention includes novel occlusive devices as well as methods of using and making these devices.

In one aspect, described herein is a vaso-occlusive device having an outer surface, the outer surface comprising a non-random texture comprising raised and depressed regions, wherein the raised regions are arranged in a repeating manner about at least a portion of such outer surface and are separated from at least one neighboring raised region by an average axial distance and an average radial distance. In certain embodiments, the vaso-occlusive device further comprises a core wire.

In another aspect, provided herein is a vaso-occlusive device having a non-random textured outer surface, the device comprising a core wire formed into a primary configuration, wherein the core wire defines at least a portion of the outer surface of the device.

In any of the devices described herein, the core wire can be textured and/or one or more filaments can be wrapped around the core wire (e.g., touching the core wire or devices in which there is a gap between the one or more filaments and the core wire).

Any of the devices (e.g., core wire and/or filaments) described herein may comprise a metal (e.g., gold, nickel, titanium, tantalum, platinum and alloys or combinations thereof). In certain embodiments, one or more filaments and/or the core wire are platinum.

In certain embodiments, the vaso-occlusive devices as described herein are a helical coil shape. Furthermore, any of the devices may have a secondary shape that self-forms upon deployment, for example, a secondary shape comprising a plurality of connected looped segments and wherein each segment lies in a different plane from the adjacent segment(s), cloverleaf shaped, helically-shaped, figure-8 shaped, flower-shaped, vortex-shaped, ovoid, randomly shaped, and substantially spherical.

Any of the devices described herein may further comprise a detachment junction (e.g., an electrolytically detachable junction, or a detachable junction that is detachable by mechanical, hydraulic, electrical, electromagnetic, thermal, or sonic means. The detachment junction can be positioned anywhere on the device, for example at one or both ends of the device. In certain embodiments, the severable junction(s) are, an electrolytically detachable assembly adapted to detach by imposition of a current; a mechanically detachable assembly adapted to detach by movement or pressure; a thermally detachable assembly adapted to detach by localized delivery of heat to the junction; a radiation detachable assembly adapted to detach by delivery of electromagnetic radiation to the junction or combinations thereof.

Furthermore, any of the devices described herein may further include one or more additional components, for example, bioactive components.

In another aspect, provided herein is a method of at least partially occluding an aneurysm, the method comprising the steps of introducing a vaso-occlusive device as described herein into the aneurysm.

In yet another aspect, described herein is a method of making a vaso-occlusive device as described herein, the method comprising the step of winding a textured core wire into a primary helical shape, thereby making a vaso-occlusive device with a textured outer surface.

In yet another aspect, provided herein is a method of making a vaso-occlusive device as described herein, the method comprising the steps of winding one or more filaments around a core wire; and winding the core wire with wound one or more filaments about a mandrel to form a microcoil, wherein at least a portion of the filaments are wound in an open pitch configuration such that the core wire defines a portion of the outer surface of the device, thereby making a vaso-occlusive device with a textured outer surface.

In yet another aspect, provided herein is a method of making a vaso-occlusive device comprising a core wire and one or more filaments, wherein there is a gap between the core wire and at least one of the filaments, the method comprising the steps of: providing a core wire that is at least partially coated with one or more dissolvable, degradable or shrinkable materials; winding one or more filaments around the core wire; and dissolving, degrading or shrinking the degradable or shrinkable material, thereby making a vaso-occlusive device having a gap between the one or more filaments and the core wire. In certain embodiments, the material is degraded upon application of heat.

In another aspect, the invention includes a method of occluding a body cavity comprising introducing any of the vaso-occlusive devices described herein into a body cavity (e.g., an aneurysm). In certain embodiments, the devices described herein can be packed into a selected target site (e.g., aneurysms).

These and other embodiments of the subject invention will readily occur to those of skill in the art in light of the disclosure herein.

BRIEF DESCRIPTION OF THE DRAWINGS

FIG. 1, panels A and B show side views of exemplary filament-wrapped wires. FIG. 1A shows an evenly spaced filament wrap. FIG. 1B shows a filament wrapped wire in which the some windings of the filament are touching.

FIG. 3, panels A to C, are a side, a cross-section and an overview, respectively, of an exemplary device with a textured surface as described herein. FIG. 3C shows an overview of the device represented in FIG. 3B.

FIG. 4, panels A and B, are side and cross-section views, respectively, of another exemplary device having a textured surface as described herein. FIG. 4A is a side-view of an exemplary embodiment in which the wire wound into the helically wound coil is a patterned wire. FIG. 4B is an axial cross-section view of the embodiment shown in FIG. 4A.

FIG. 5, panels A and B, are side and cross-section views, respectively, of another exemplary device with a textured surface as described herein.

DETAILED DESCRIPTION

Figure 2:
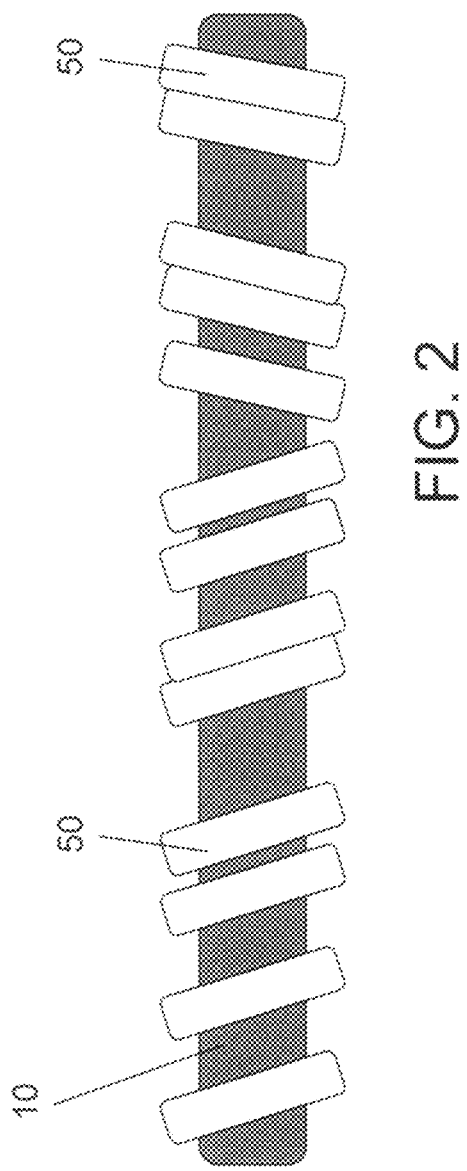
FIG. 2 shows a side view of exemplary filament wrapped wire. The filament itself comprises a cable-wound filament. The filament is wrapped around the wire in an irregular pitch and in different (s and z) directions.

Occlusive (e.g., embolic) devices are described. The devices described herein find use in vascular and neurovascular indications and are particularly useful in treating aneurysms, for example small-diameter, curved or otherwise difficult to access vasculature, for example aneurysms, such as cerebral aneurysms. Methods of making and using these vaso-occlusive devices also form aspects of this invention. The compositions and methods described herein may achieve better occlusion and treatment outcomes (e.g., long term durability) than known devices, for example, because the textured surfaces facilitate tissue in-growth, the increased surface area results in a greater tissue reactivity; and/or the surface patterning may also create disturbances in blood flow which may facilitate the development of more durable clots (e.g., clots that are less susceptible to fibrinolytic breakdown). In addition, devices with engineered textures disposed on the outer surfaces as described herein tend to have relatively low-friction surfaces when compared to traditional methods of surface texturing such as abrasive treatments, porous coatings, and multi-filament wrappings.

Thus, advantages of the present invention include, but are not limited to, (i) the provision of low-friction vaso-occlusive devices; (ii) the provision of occlusive devices that can be packed into aneurysms at high densities; (iii) the provision of occlusive devices having improved exposure of the surface(s) of the components to blood flow; (iv) the provision of occlusive devices that do not catch or adversely interact with the delivery catheter; (vi) the provision of occlusive devices that can be retrieved and/or repositioned after deployment; and (vii) cost-effective production of these devices.

All publications, patents and patent applications cited herein, whether above or below, are hereby incorporated by reference in their entirety.

It must be noted that, as used in this specification and the appended claims, the singular forms "a", "an", and "the" include plural referents unless the content clearly dictates otherwise. Thus, for example, reference to a device comprising "a filament" includes devices comprising of two or more filaments.

The vaso-occlusive devices described herein have a three-dimensional textured surface. Preferably the textured outer surface has a non-random texture. "Non-random" includes any ordered or semi-ordered structure that provides texture to the outer surface. For example, the non-random textured surface may comprise raised and depressed regions wherein the raised regions are arranged in a repeating manner about the outer surface and separated from neighboring raised elements by an average distance. Thus, unlike randomly textured devices, such as sandblasted devices (see, U.S. Pat. No. 6,953,468), the devices described herein have a non-random texture on the outer surface.

In order to generate a surface texture capable of providing maximal biological contact and maintaining low friction the patterns would preferably comprise depressed regions in the form of gaps, channels, valleys, or voids wherein the smallest regular (repeated) distance between the raised regions is smaller than the smallest regular (repeated) dimension of the raised regions. Preferably the smallest regular (repeated) distance between the raised regions would be in the range of 2-100 microns, more preferably from 10-40 microns.

The textured surface may be created by profiling or patterning a wire and forming a vaso-occlusive device, by profiling or patterning an already formed vaso-occlusive device, and/or by disposing one or more filaments around the outer surface of a core wire, such that the outer surface of the device is defined by both the outer surface of the core wire and the outer surface of the filament(s). By "filament" is meant any long, thin structure that has a small cross-section. Thus, as used herein, the term includes monofilaments as well as multi-filaments (e.g., multifilament yarns, threads or sutures) and further includes filaments having any cross-sectional profile (circular, oval, triangular, rectangular, etc.). In addition, the filament itself may be a multi-filament wind, for example cable-wound (s or z-wound) filaments. See, e.g., FIG. 2. The filament may be wound in a regular or irregular pitch and in either direction (S or Z winds). Furthermore, some winds may not include a gap therebetween (FIG. 1).

When present, the core wire, device and optional filament(s) can be made of any material, including, but not limited to, metals and/or polymers (see below). In certain embodiments, the device is "metallic" in that it is comprised solely of metals (or metal alloys) and does not include any polymers. Non-limiting examples of metals include any biologically compatible metal or metal alloy such as the Platinum Group metals, especially platinum, rhodium, palladium, rhenium, as well as tungsten, gold, silver, tantalum, and alloys of these metals. Suitable "super-elastic alloys" include nickel/titanium alloys (48-58 atomic % nickel and optionally containing modest amounts of iron); copper/zinc alloys (38-42 weight % zinc); copper/zinc alloys containing 1-10 weight % of beryllium, silicon, tin, aluminum, or gallium; or nickel/aluminum alloys (36-38 atomic % aluminum). See, e.g., U.S. Pat. Nos. 3,174,851; 3,351,463; and 3,753,700. Especially preferred is the titanium/nickel alloy known as Nitinol™. These are very sturdy alloys that will tolerate significant flexing without deformation even when used as a very small diameter filament. In a preferred embodiment, the metal wire (patterned or filament-wrapped) is wound into a primary helical shape. The wire may be, but is not necessarily, subjected to a heating step to set the wire into the primary shape.

The diameter of the wire is often in a range of 0.0005 and 0.050 inches, preferably between about 0.001 and about 0.004 inches in diameter. Similarly, the diameter of the filaments is typically in the range of 0.0003 and 0.005 inches, more preferably from 0.00050 to 0.00075 inches. Preferably, the diameter of the filament is more than the diameter of gap (pitch) created when the filament is wound around the core wire. Determining suitable filament diameter(s), pitch (spacing between winds) and/or direction of filament wrap (z and/or s) and primary wire wind (Z and/or S) are within the purview of the skilled artisan.

The core wire itself may have a uniform cross-section or, alternatively, may have a non-uniform cross-section by virtue of a textured surface (FIG. 4). By "textured" or "patterned" is meant any core wire that has a non-uniform cross-section, for example a wire having indentations (regular or irregular) therein, roughened portions, patterns, or any other modifications that result in a wire with a textured outer surface.

Furthermore, with respect to the device as a whole, the overall cross-section of the devices described herein is not uniform or constant. See, e.g., FIGS. 3B, 4B and 5B. For example, in the embodiments shown in FIGS. 3B and 5B, the surfaces of both the wire and filaments are exposed when the device is implanted into the vasculature. Likewise, the non-uniform surface of the indented (patterned) wire shown in FIGS. 4A and 4B, also creates a textured surface when the wire is wound into a primary helical coil configuration. The textured outer surface of the device promotes tissue ingrowth and/or reduces friction.

When present, the filament(s) may be adhered to the core wire in one or more locations, for example by heating or by use of adhesives (e.g., EVA) to the filament or to the core wire) or by other suitable means. The filament(s) may be secured at multiple locations on the core wire, for example, at one or both ends. Alternatively, the filaments may not be secured (attached) to the underlying core wire. In still other embodiments, a layer of a degradable polymer is positioned between the filament(s) and the core wire.

In certain embodiments, the device changes shape (configuration) upon deployment, for example change from a constrained linear form to a relaxed, three-dimensional (secondary) configuration. See, also, U.S. Pat. No. 6,280,457. Methods of making metallic and/or polymeric vaso-occlusive coils having a linear helical shape and/or a different three-dimensional (secondary) configuration are known in the art and described in detail in the documents cited above, for example in U.S. Pat. No. 6,280,457. Thus, it is further within the scope of this invention that the vaso-occlusive devices as a whole or elements thereof comprise secondary shapes or structures that differ from the linear coil shapes depicted in the Figures, for examples, overlapping and non-overlapping spheres, ellipses, spirals, ovoids, figure-8 shapes, etc. See, e.g., U.S. Pat. Nos. 6,635,069 and 6,929,654. The devices described herein may be self-forming in that they assume the secondary configuration upon deployment into an aneurysm. Alternatively, the devices may assume their secondary configurations under certain conditions (e.g., change in temperature, application of energy, etc.).

Additionally, stretch-resistant configurations can also be designed and manufactured. For example, a fiber material can be threaded through the inside of the device and secured to both the proximal and distal end of the device. See, e.g., U.S. Pat. No. 6,280,457.

Furthermore, it will be apparent that the core wire can be wound into a primary (linear) and/or secondary configuration before or after it is combined with the filament(s) (e.g., pre-formed filament structure or winding of filaments). For example, the filament(s) can be added to an already shaped core wire, for example by loading the filament(s) onto an underlying core wire that has been wound into a helical coil, securing the filaments to the underlying shaped core wire at one or more locations (e.g., by using ultraviolet glue to fix the ends of the filament structure and optionally heat setting the device so shrink the filament structure to the underlying shaped (e.g., coiled) wire). Thus, the winding, braiding, weaving, etc., may be performed in the absence of the core wire and, subsequently, the already-configured filament structure may be combined with a core wire. Non-limiting examples of such filament structures include braids, woven structure, tubular configurations, non-woven materials (e.g., felt-like materials) and the like. Such pre-formed filament structures may be attached in any manner to the core wire at one or more locations. For example, in certain embodiments, the pre-formed filament structure is attached by its ends to the core wire (e.g., to the ends of core wire).

FIG. 1 depicts a filament 50 wrapped around a core wire 10. As depicted in FIG. 1A the filaments may be regularly spaced, or as in FIG. 1B, some of the filament 50 windings can be adjacent, so long as, when the device is formed, at least a portion of the core wire 10 defines a part of the outer surface of the overall device.

FIG. 2 depicts a cable-wound filament 50 wound around a core wire 10. As depicted in this figure, the filament 50 windings can be irregular, for example some windings can be adjacent and some can be separated. In addition, FIG. 2 depicts how the filament 50 can be wound in different directions along the length of the wire.

Figure 3A:
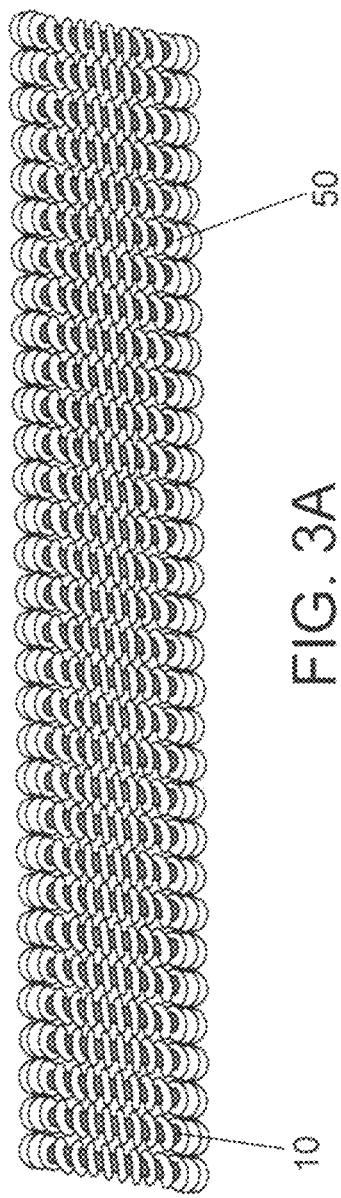
FIG. 3A shows a side-view of an embodiment in which the core wire is wrapped with one or more filaments in an open, regularly-spaced pitch.
Figure 3B:
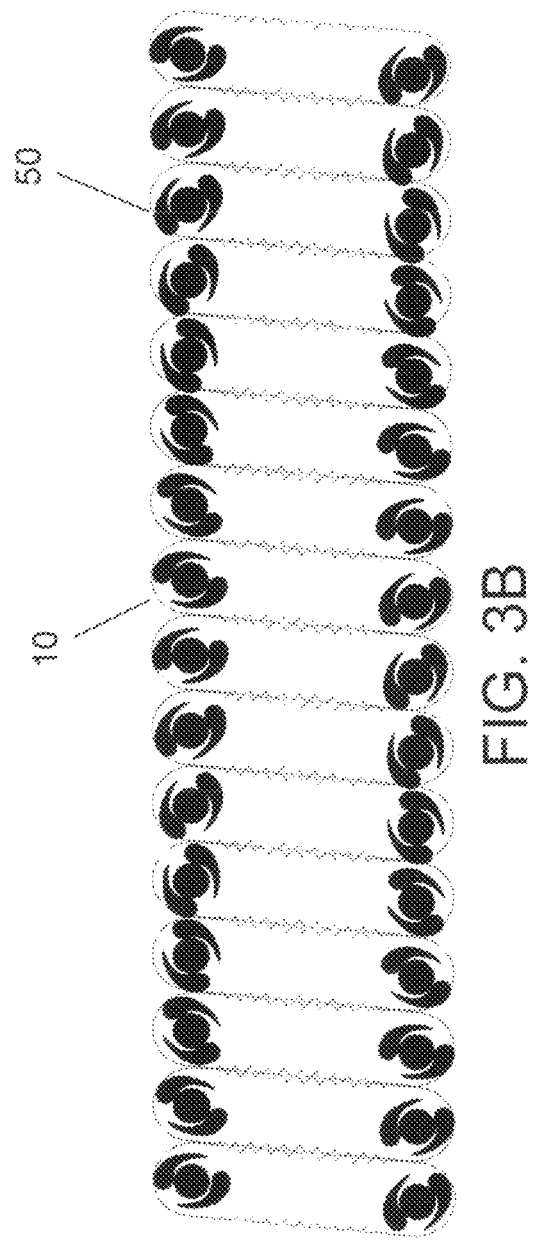
FIG. 3B is an axial cross-section view of a device in which a core wire is wrapped with two filaments and the wrapped core wire is wound into helical coil.

FIG. 3A shows an embodiment in which a filament 50 is spirally wound around a core wire 10. The filament and core wire are preferably metal, for example platinum. The filament 50 is wound around the core wire 10 in such a way that at least a portion of the core wire 10 forms part of the outer surface of the device when the filament wrapped wire is formed into a primary helical configuration. Furthermore, although the filament shown in FIG. 3A is wound in regular pitch spacing, it will be apparent that the irregular pitch windings are also contemplated. FIG. 3B shows an axial cross-section of the device shown in FIG. 3A and illustrates that the spirally wound elements and the device as a whole have a non-uniform cross-sections resulting in a textured outer surface. FIG. 3C is an overview depicting the filament-wrapped wire wound into a helical coil and shows raised 40 and depressed 60 regions created by wrapping two filaments 50, 55 around the core wire 10. A single filament or more than two filaments (e.g. three or more) can also be wound around the core wire.

FIG. 4A shows a device in which a patterned core wire 10 is formed into a helically wound coil. In a preferred embodiment, the core wire is, for example platinum. The embodiment depicted shows a regular patterning (indentation) profile. Irregular patterning profiles are also contemplated. The axial cross-section of the device, as shown in FIG. 4B, is irregular and results in a device having a textured outer surface.

Figure 5A:
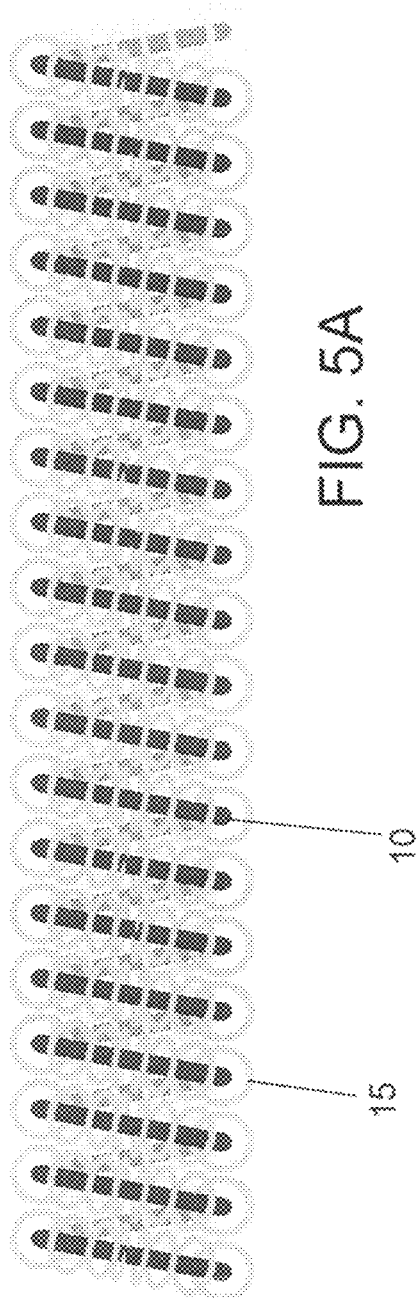
FIG. 5A depicts a side-view of a device comprising a wire wrapped, in an open, regularly-spaced pitch, with one or more filaments such that at least some of the filaments do not contact the core wire.
Figure 5B:
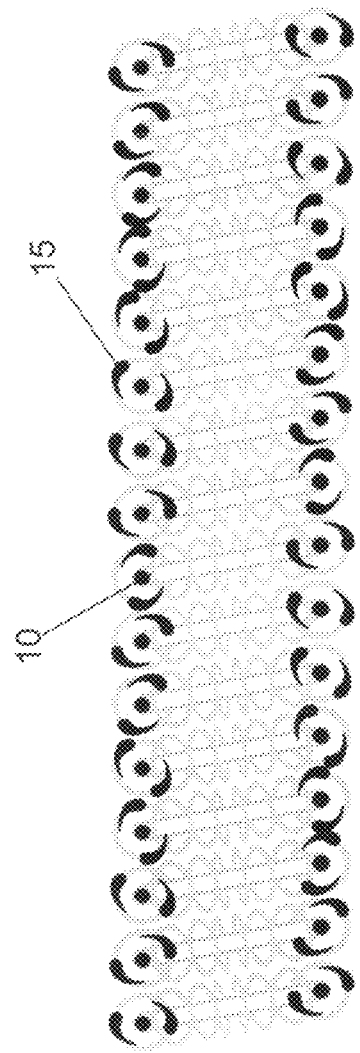
FIG. 5B is an axial cross-section view of the device.

FIG. 5A depicts a device in which there is a gap between the filament 15 and the core wire 10. The distance between the filament 15 and core wire 10 can be constant or can vary along the length of the device. For example, in one or more regions the filament 15 may contact the core wire.

A device including at least some space between the filament and the core wire (see, e.g., FIG. 5A) can be made in a variety of ways. For example, in certain embodiments, a metallic core wire is coated with a dissolvable, degradable or shrinkable material (e.g., polymer). Subsequently, a metallic filament is wound around the coated core wire. When the resulting device is subjected to conditions that dissolve, degrade or shrink the coating material, the coating material is eliminated or reduced so as to leave a space between the core wire and filament. Non-limiting examples of conditions that dissolve, degrade or shrink the coating material include, exposure to heat (thermal energy), exposure to solvents that degrade or shrink the coating material and the like. In other embodiments, the filament may be wound around the core wire (before or after the wire is wound into its primary configuration such as a helically wound coil) such that at least areas of the filament do not contact the wire.

Non-limiting examples of dissolvable, degradable or shrinkable synthetic and natural polymers, include polyurethanes (including block copolymers with soft segments containing esters, ethers and carbonates), polyethers, polyamides (including nylon polymers and their derivatives), polyimides (including both thermosetting and thermoplastic materials), acrylates (including cyanoacrylates), epoxy adhesive materials (two part or one part epoxy-amine materials), olefins (including polymers and copolymers of ethylene, propylene butadiene, styrene, and thermoplastic olefin elastomers), fluoronated polymers (including polytetrafluoroethylene (ePTFE or PTFE)), polyethylene teraphthalate (PET), polydimethyl siloxane-based polymers, cross-linked polymers, non-cross linked polymers, Rayon, cellulose, cellulose derivatives such nitrocellulose, natural rubbers, polyesters such as lactides, glycolides, trimethylene carbonate, caprolactone polymers and their copolymers, hydroxybutyrate and polyhydroxyvalerate and their copolymers, polyether esters such as polydioxinone, anhydrides such as polymers and copolymers of sebacic acid, hexadecandioic acid and other diacids, or orthoesters.

Polymeric components may include one or more absorbable (biodegradable) polymers and/or one or more non-absorbable polymers. The terms "absorbable" and "biodegradable" are used interchangeable to refer to any agent that, over time, is no longer identifiable at the site of application in the form it was injected, for example having been removed via degradation, metabolism, dissolving or any passive or active removal procedure. Non-limiting examples of absorbable proteins include synthetic and polysaccharide biodegradable hydrogels, collagen, elastin, fibrinogen, fibronectin, vitronectin, laminin and gelatin. Many of these materials are commercially available. Fibrin-containing compositions are commercially available, for example from Baxter. Collagen containing compositions are commercially available, for example from Cohesion Technologies, Inc., Palo Alto, Calif. Fibrinogen-containing compositions are described, for example, in U.S. Pat. Nos. 6,168,788 and 5,290,552. Mixtures, copolymers (both block and random) of these materials are also suitable. Furthermore, it will be apparent that combinations of metals and one or more polymeric components may be used in any way, for example coated metals, coated polymer(s), etc. Coatings preferably leave the underlying surface pattern intact or revert to the surface pattern after deployment.

Figure 6B:
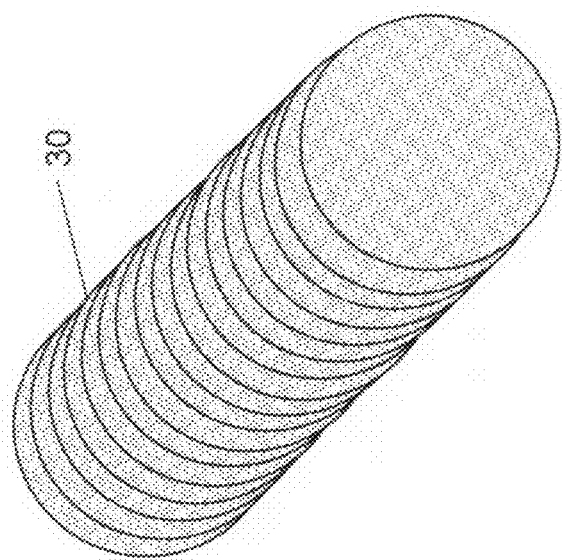
FIG. 6, panels A and B, are overview and partial cross-section views of non-textured and randomly textured devices.
FIG. 6A depicts a coil device with no texturing and 6B depicts a coil device with random texturing.
Figure 6A:
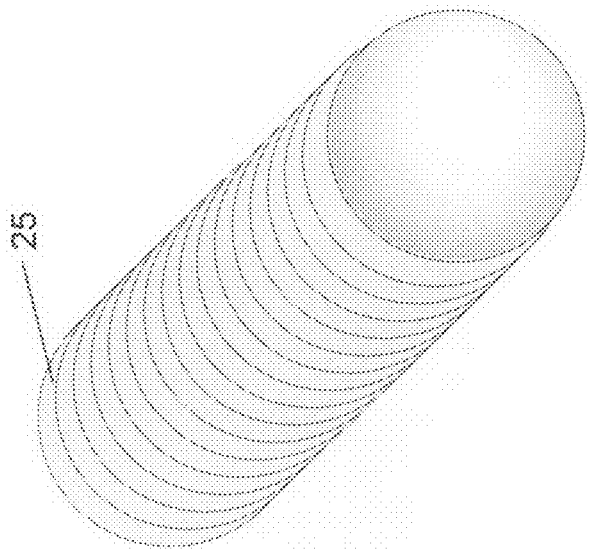
Figure 7F:
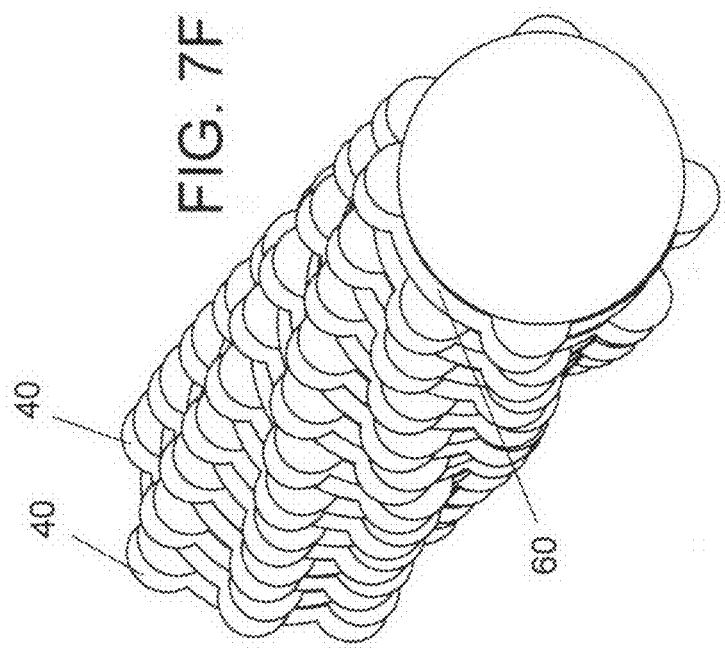
FIG. 7, panels A to F, are overviews of exemplary non-randomly textured occlusive devices as described herein.
Figure 7E:
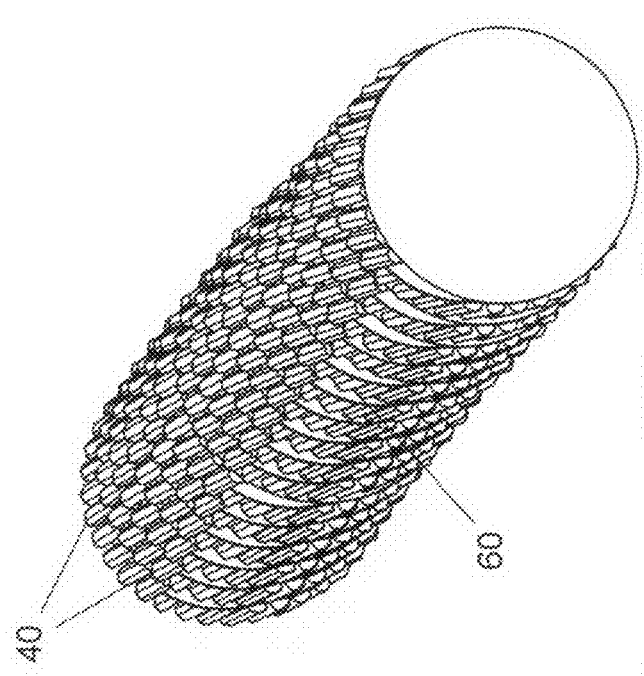

FIG. 6A shows a coil device in which is non-textured or very simply textured. The coil winds 25 create a single raised helical region in the outer surface of the device. This construction is known in the art and is analogous to most bare metal embolic coils currently used in the clinic. It should be noted that this configuration possesses only one raised region and therefore has no repeating pattern of discrete raised regions and is therefore distinctly different than the repeating textures claimed herein.

FIG. 6B shows the device of FIG. 6A in which the outer surface 30 is randomly textured. It will be apparent that the outer surface may have a random textured overlaid on simple coil device, for example by sandblasting a coil device as shown in FIG. 6A. The device shown in FIG. 6B may also be formed from a randomly textured substance and subsequently coiled to form the device. This randomly textured configuration does not possess a non-random repeating pattern of discrete raised regions and if therefore distinctly different than the repeating textures claimed herein.

Figure 8:
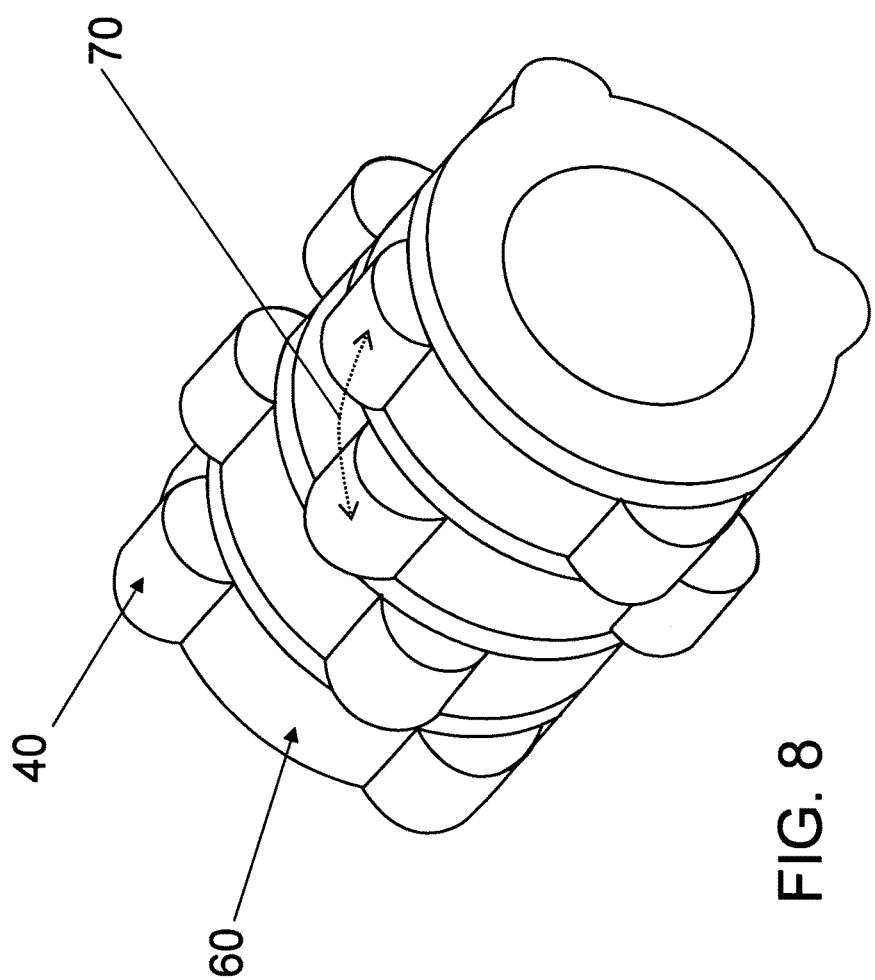
FIG. 8 is an overview and partial cross-section view of another exemplary device having a non-randomly textured outer surface.

FIGS. 7A to 7F show various devices with non-randomly textured outer surfaces having raised 40 and depressed 60 regions on the outer surface of the devices. FIG. 8 depicts another exemplary non-randomly textured device and also shows how the raised regions are arranged in a repeating manner about the outer surface of the devices such that they are separated from one or more neighboring raised elements by an average axial distance and an average radial distance 70. As shown in FIGS. 7 and 8, the raised regions may be separated from one, two or more of the neighboring raised regions by an average distance. For example, as shown in FIG. 7A to 7F, the spacing of the raised regions is relatively even as compared to all neighboring raised regions (in all directions). FIG. 8 shows an example in which any given raised region is separated from the diagonally neighboring raised regions by a different average distance than it is separated from the laterally (e.g., in the same cross-sectional "row") neighboring raised regions.

Any of the devices described herein may also comprise additional components (described in further detail below), such as co-solvents, plasticizers, radio-opaque materials (e.g., metals such as tantalum, gold or platinum), coalescing solvents, bioactive agents, antimicrobial agents, antithrombogenic agents, antibiotics, pigments, radiopacifiers and/or ion conductors which may be coated using any suitable method or may be incorporated into the element(s) during production. In addition, lubricious materials (e.g., hydrophilic) materials may be used to coat one or more members of the device to help facilitate delivery. Cyanoacrylate resins (particularly n-butylcyanoacrylate), particular embolization materials such as microparticles of polyvinyl alcohol foam may also be introduced into the intended site after the inventive devices are in place.

The term "bioactive" refers to any agent that exhibits effects in vivo, for example a thrombotic agent, an anti-thrombotic agent (e.g., a water-soluble agent that inhibits thrombosis for a limited time period, described above), a therapeutic agent (e.g., chemotherapeutic agent) or the like. See, e.g., co-owned U.S. Pat. No. 6,585,754 and WO 02/051460. Non-limiting examples of bioactive materials include cytokines; extracellular matrix molecules (e.g., collagen); trace metals (e.g., copper); and other molecules that stabilize thrombus formation or inhibit clot lysis (e.g., proteins or functional fragments of proteins, including but not limited to Factor XIII, $\alpha_2$-antiplasmin, plasminogen activator inhibitor-1 (PAI-1) or the like). Non-limiting examples of cytokines which may be used alone or in combination in the practice of the present invention include, basic fibroblast growth factor (bFGF), platelet derived growth factor (PDGF), vascular endothelial growth factor (VEGF), transforming growth factor beta (TGF-β) and the like. Cytokines, extracellular matrix molecules and thrombus stabilizing molecules (e.g., Factor XIII, PAI-1, etc.) are commercially available from several vendors such as, for example, Genzyme (Framingham, Mass.), Genentech (South San Francisco, Calif.), Amgen (Thousand Oaks, Calif.), R&D Systems and Immunex (Seattle, Wash.). Additionally, bioactive polypeptides can be synthesized recombinantly as the sequences of many of these molecules are also available, for example, from the GenBank database. Thus, it is intended that the invention include use of DNA or RNA encoding any of the bioactive molecules. Cells (e.g., fibroblasts, stem cells, etc.) can also be included. Such cells may be genetically modified. Furthermore, it is intended, although not always explicitly stated, that molecules having similar biological activity as wild-type or purified cytokines, extracellular matrix molecules and thrombus-stabilizing proteins (e.g., recombinantly produced or mutants thereof) and nucleic acid encoding these molecules are intended to be used within the spirit and scope of the invention. Further, the amount and concentration of liquid embolic and/or other bioactive materials useful in the practice of the invention can be readily determined by a skilled operator and it will be understood that any combination of materials, concentration or dosage can be used, so long as it is not harmful to the subject.

The devices described herein are often introduced into a selected site using the procedure outlined below. This procedure may be used in treating a variety of maladies. For instance in the treatment of an aneurysm, the aneurysm itself will be filled (partially or fully) with the compositions described herein.

Conventional catheter insertion and navigational techniques involving guidewires or flow-directed devices may be used to access the site with a catheter. The mechanism will be such as to be capable of being advanced entirely through the catheter to place vaso-occlusive device at the target site but yet with a sufficient portion of the distal end of the delivery mechanism protruding from the distal end of the catheter to enable detachment of the implantable vaso-occlusive device. For use in peripheral or neural surgeries, the delivery mechanism will normally be about 100-200 cm in length, more normally 130-180 cm in length. The diameter of the delivery mechanism is usually in the range of 0.25 to about 0.90 mm. Briefly, occlusive devices (and/or additional components) described herein are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the embolics (e.g. vaso-occlusive members and/or liquid embolics and bioactive materials) which cause formation of an emboli and, at some later time, is at least partially replaced by neovascularized collagenous material formed around the implanted vaso-occlusive devices.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter. Once the distal end of the catheter is positioned at the site, often by locating its distal end through the use of radiopaque marker material and fluoroscopy, the catheter is cleared. For instance, if a guidewire has been used to position the catheter, it is withdrawn from the catheter and then the assembly, for example including the absorbable vaso-occlusive device at the distal end, is advanced through the catheter.

Once the selected site has been reached, the vaso-occlusive device is extruded, for example by loading onto a pusher wire. Preferably, the vaso-occlusive device is loaded onto the pusher wire via a mechanically or electrolytically cleavable junction (e.g., a GDC-type junction that can be severed by application of heat, electrolysis, electrodynamic activation or other means). Additionally, the vaso-occlusive device can be designed to include multiple detachment points, as described in co-owned U.S. Pat. Nos. 6,623,493 and 6,533,801 and International Patent publication WO 02/45596. They are held in place by gravity, shape, size, volume, magnetic field or combinations thereof.

It will also be apparent that the operator can remove or reposition (distally or proximally) the device. For instance, the operator may choose to insert a device as described herein, before detachment, move the pusher wire to place the device in the desired location.

Modifications of the procedure and vaso-occlusive devices described above, and the methods of using them in keeping with this invention will be apparent to those having skill in this mechanical and surgical art. These variations are intended to be within the scope of the claims that follow.

What is claimed is:

1. An occlusive device having an outer surface, the outer surface comprising a continuous, non-randomly textured material defining raised and depressed regions, wherein the raised regions are arranged in a repeating manner about at least a portion of such outer surface and are separated from neighboring raised regions by uniform axial distance and a uniform radial distance, wherein the raised regions are gradually concave and taper to a rounded point projecting away from the surface.

2. The occlusive device of claim 1, further comprising a core wire.

3. The occlusive device of claim 1, wherein the device comprises a metal selected from the group consisting of gold, nickel, titanium, tantalum, platinum and alloys thereof.

4. The occlusive device of claim 1, wherein the device is a helical coil.

5. The occlusive device of claim 1, wherein the device has a secondary shape that self-forms upon deployment.

6. The occlusive device of claim 5, wherein the secondary shape comprises a plurality of connected looped segments and wherein each segment lies in a different plane from an adjacent segment.

7. The occlusive device of claim 5, where the secondary shape is selected from the group consisting of cloverleaf shaped, helically-shaped, figure-8 shaped, flowershaped, vortex-shaped, ovoid, randomly shaped, and substantially spherical.

8. The occlusive device of claim 1, further comprising a detachment junction.

9. The occlusive device of claim 8, wherein the detachable junction is detachable by mechanical, hydraulic, electrical, electromagnetic, thermal, or sonic means.

10. A method of at least partially occluding an aneurysm, comprising introducing an occlusive device according to claim 1 into the aneurysm.

* * * * *